United States Patent
Ben Nun (10) Patent No.: US 7,842,087 B2
(45) Date of Patent: Nov. 30, 2010

(54) ACCOMMODATING INTRAOCULAR LENS ASSEMBLIES AND ACCOMMODATION MEASUREMENT IMPLANT

(75) Inventor: Yehoshua Ben Nun, D.N. Vitkin (IL)

(73) Assignee: NuLens Ltd., Herzliya (IL)

( * ) Notice: Subject to any disclaimer, the term of this patent is extended or adjusted under 35 U.S.C. 154(b) by 860 days.

(21) Appl. No.: 11/568,416

(22) PCT Filed: May 1, 2005

(86) PCT No.: PCT/IL2005/000456

§ 371 (c)(1),
(2), (4) Date: Oct. 27, 2006

(87) PCT Pub. No.: WO2005/104994

PCT Pub. Date: Nov. 10, 2005

(65) Prior Publication Data

US 2008/0004699 A1     Jan. 3, 2008

Related U.S. Application Data

(60) Provisional application No. 60/589,567, filed on Jul. 21, 2004.

(30) Foreign Application Priority Data

Apr. 29, 2004   (IL) .................................... 161706

(51) Int. Cl.
*A61F 2/16* (2006.01)
(52) U.S. Cl. ................................... 623/6.37
(58) Field of Classification Search ............... 623/4.1, 623/6.11, 6.12, 6.14, 6.15, 6.18, 6.19, 6.2, 623/6.21, 6.22, 6.24, 6.27, 6.34, 6.37, 6.38, 623/6.39, 6.4, 6.41, 6.42, 6.43, 6.44, 6.45, 623/6.46, 6.47, 6.49, 6.51, 6.54
See application file for complete search history.

(56) References Cited

U.S. PATENT DOCUMENTS

| 3,950,082 A | 4/1976 | Volk |
| 4,122,556 A | 10/1978 | Poler |
| 4,254,509 A | 3/1981 | Tennant |
| 4,298,994 A | 11/1981 | Clayman |

(Continued)

FOREIGN PATENT DOCUMENTS

EP    0 156 472 A    2/1985

(Continued)

OTHER PUBLICATIONS

U.S. Appl. No. 11/568,416, Nun.

(Continued)

*Primary Examiner*—David Isabella
*Assistant Examiner*—Joshua Levine
(74) *Attorney, Agent, or Firm*—Morgan, Lewis & Bockius LLP (57) ABSTRACT

The present invention pertains to accommodating intraocular lens (AIOL) assemblies including a haptics system for self-anchoring implantation in a human eye's annular ciliary sulcus for retaining an AIOL at a desired position along the human eye's visual axis, and an accommodation measurement implant (AMI) for determining accommodation and accommodation forces in an experimental set-up including an animal's eye.

25 Claims, 7 Drawing Sheets

U.S. PATENT DOCUMENTS

| | | | |
|---|---|---|---|
| 4,340,979 | A | 7/1982 | Kelman |
| 4,409,690 | A | 10/1983 | Gess |
| 4,409,691 | A | 10/1983 | Levy |
| 4,445,998 | A | 5/1984 | Kanda et al. |
| 4,446,581 | A | 5/1984 | Blake |
| 4,494,254 | A | 1/1985 | Lopez |
| 4,530,117 | A | 7/1985 | Kelman |
| RE31,963 | E | 8/1985 | Kelman |
| 4,556,998 | A | 12/1985 | Siepser |
| 4,581,033 | A | 4/1986 | Callahan |
| 4,589,147 | A | 5/1986 | Nevyas |
| 4,591,358 | A | 5/1986 | Kelman |
| 4,615,701 | A | 10/1986 | Woods |
| 4,671,283 | A | 6/1987 | Hoskin et al. |
| 4,676,794 | A | 6/1987 | Kelman |
| 4,750,904 | A | 6/1988 | Price, Jr. |
| 4,808,181 | A | 2/1989 | Kelman |
| 4,842,601 | A | 6/1989 | Smith |
| RE33,039 | E | 8/1989 | Arnott |
| 4,865,601 | A | 9/1989 | Caldwell et al. |
| 4,888,012 | A | 12/1989 | Horn et al. |
| 4,892,543 | A | 1/1990 | Turley |
| 4,932,966 | A | 6/1990 | Christie et al. |
| 4,932,968 | A | 6/1990 | Caldwell et al. |
| 4,957,505 | A | 9/1990 | McDonald |
| 4,969,897 | A | 11/1990 | Kalb |
| 4,976,732 | A | 12/1990 | Vorosmarthy |
| 4,990,159 | A | 2/1991 | Kraff |
| 5,078,742 | A | 1/1992 | Dahan |
| 5,171,268 | A | 12/1992 | Ting et al. |
| 5,176,701 | A | 1/1993 | Dusek et al. |
| 5,275,623 | A | 1/1994 | Sarfarazi |
| 5,282,851 | A | 2/1994 | Jacob-LaBarre |
| 5,288,293 | A | 2/1994 | O'Donnell, Jr. |
| 5,336,262 | A | 8/1994 | Chu |
| 5,346,502 | A | 9/1994 | Estabrook et al. |
| 5,476,512 | A | 12/1995 | Sarfarazi |
| 5,476,514 | A | 12/1995 | Cumming |
| 5,476,515 | A | 12/1995 | Kelman et al. |
| 5,480,426 | A | 1/1996 | Chu |
| 5,484,447 | A | 1/1996 | Waldock et al. |
| 5,489,302 | A | 2/1996 | Skottun |
| 5,496,366 | A | 3/1996 | Cumming |
| 5,522,891 | A | 6/1996 | Klaas et al. |
| 5,567,365 | A | 10/1996 | Weinschenk et al. |
| 5,571,177 | A | 11/1996 | Deacon et al. |
| 5,607,472 | A | 3/1997 | Thompson |
| 5,628,795 | A | 5/1997 | Langerman |
| 5,674,282 | A | 10/1997 | Cumming |
| 5,684,637 | A | 11/1997 | Floyd |
| 5,722,952 | A | 3/1998 | Schachar |
| 5,752,960 | A | 5/1998 | Nallakrishnan |
| 5,766,244 | A | 6/1998 | Binder et al. |
| 5,843,188 | A | 12/1998 | McDonald |
| 5,871,455 | A | 2/1999 | Ueno et al. |
| 5,919,230 | A | 7/1999 | Sambursky |
| 5,968,094 | A | 10/1999 | Werblin et al. |
| 6,007,579 | A * | 12/1999 | Lipshitz et al. ............ 623/6.11 |
| 6,051,024 | A | 4/2000 | Cumming |
| 6,110,202 | A | 8/2000 | Barraquer et al. |
| 6,117,171 | A | 9/2000 | Skottun |
| 6,129,759 | A | 10/2000 | Chambers |
| 6,164,282 | A | 12/2000 | Gwon et al. |
| 6,197,057 | B1 | 1/2001 | Peyman et al. |
| 6,193,750 | B1 | 2/2001 | Cumming |
| 6,197,059 | B1 | 3/2001 | Cumming |
| 6,200,342 | B1 | 3/2001 | Tassignon et al. |
| 6,280,469 | B1 | 8/2001 | Terry et al. |
| 6,280,471 | B1 | 8/2001 | Peyman et al. |
| 6,299,618 | B1 | 10/2001 | Sugiura |
| 6,299,641 | B1 | 10/2001 | Woods |
| 6,342,073 | B1 | 1/2002 | Cumming et al. |
| 6,387,126 | B1 | 5/2002 | Cumming |
| 6,406,494 | B1 | 6/2002 | Laguette et al. |
| 6,423,094 | B1 | 7/2002 | Sarfarazi |
| 6,443,984 | B1 | 9/2002 | Jahn et al. |
| 6,443,985 | B1 | 9/2002 | Woods |
| 6,464,725 | B2 | 10/2002 | Skotton |
| 6,488,708 | B2 | 12/2002 | Sarfarazi |
| 6,494,910 | B1 | 12/2002 | Ganem et al. |
| 6,494,911 | B2 | 12/2002 | Cumming |
| 6,503,276 | B2 | 1/2003 | Lang et al. |
| 6,506,212 | B2 | 1/2003 | Zhou et al. |
| 6,520,691 | B2 | 2/2003 | Nomura et al. |
| 6,554,860 | B2 | 4/2003 | Hoffmann et al. |
| 6,570,718 | B2 | 5/2003 | Nomura et al. |
| 6,596,026 | B1 | 7/2003 | Gross et al. |
| 6,599,317 | B1 | 7/2003 | Weinschenk, III et al. |
| 6,605,093 | B1 | 8/2003 | Blake |
| 6,616,692 | B1 | 9/2003 | Glick et al. |
| 6,638,305 | B2 | 10/2003 | Laguette |
| 6,638,306 | B2 | 10/2003 | Cumming |
| 6,645,245 | B1 | 11/2003 | Preussner |
| 6,739,722 | B2 | 5/2004 | Laguette et al. |
| 6,749,634 | B2 | 6/2004 | Hanna et al. |
| 6,790,232 | B1 | 9/2004 | Lang |
| 6,849,091 | B1 | 2/2005 | Cumming |
| 6,960,231 | B2 | 11/2005 | Tran |
| 7,008,449 | B2 | 3/2006 | Willis et al. |
| 7,037,338 | B2 | 5/2006 | Nagamoto et al. |
| 7,097,660 | B2 | 8/2006 | Portney |
| 7,118,597 | B2 | 10/2006 | Miller et al. |
| 7,122,053 | B2 | 10/2006 | Esch |
| 7,137,994 | B2 | 11/2006 | De Juan, Jr. |
| 7,220,279 | B2 | 5/2007 | Nun et al. |
| 7,261,737 | B2 | 8/2007 | Esch et al. |
| 7,278,739 | B2 | 10/2007 | Shadduck |
| 7,350,916 | B2 | 4/2008 | Hong et al. |
| 2002/0103535 | A1 | 8/2002 | Portney |
| 2002/0103537 | A1 | 8/2002 | Willis et al. |
| 2003/0060881 | A1 | 3/2003 | Glick et al. |
| 2003/0097177 | A1 | 5/2003 | Tran |
| 2003/0109926 | A1 | 6/2003 | Portney |
| 2003/0149480 | A1 | 8/2003 | Shadduck |
| 2004/0073304 | A1 | 4/2004 | Weinschenk, III et al. |
| 2004/0148022 | A1 | 7/2004 | Eggleston |
| 2004/0169816 | A1 | 9/2004 | Esch |
| 2005/0090896 | A1 | 4/2005 | Ben Nun |
| 2005/0177229 | A1 | 8/2005 | Boxer Wachle |
| 2006/0069433 | A1 | 3/2006 | Nun |
| 2006/0074487 | A1 | 4/2006 | Gilg |
| 2007/0027538 | A1 | 2/2007 | Aharoni et al. |
| 2007/0088433 | A1 | 4/2007 | Esch et al. |
| 2007/0129799 | A1 | 6/2007 | Schedler |
| 2007/0185574 | A1 | 8/2007 | Ben Nun |
| 2007/0244561 | A1 | 10/2007 | Ben Nun |
| 2008/0004699 | A1 | 1/2008 | Ben Nun |
| 2008/0188930 | A1 | 8/2008 | Mentak et al. |
| 2009/0264998 | A1 | 10/2009 | Mentak et al. |

FOREIGN PATENT DOCUMENTS

| | | |
|---|---|---|
| EP | 1321112 | 6/2003 |
| FR | 2 794 965 | 6/1999 |
| JP | 2005007029 | 1/2005 |
| TW | 523408 | 3/2003 |
| WO | WO 83/00998 | 3/1983 |
| WO | WO 94/28825 | 12/1994 |
| WO | WO-95/20367 | 8/1995 |
| WO | WO 98/05273 | 2/1998 |
| WO | WO 98/10717 | 3/1998 |
| WO | WO-9962434 | 12/1999 |
| WO | WO-0030566 | 6/2000 |
| WO | WO-00/61036 | 10/2000 |

| WO | WO-00/66037 | 11/2000 |
| --- | --- | --- |
| WO | WO 01/08606 | 2/2001 |
| WO | WO-01/60286 | 8/2001 |
| WO | WO-02065951 | 8/2002 |
| WO | WO 03/000154 | 1/2003 |
| WO | WO-03015669 | 2/2003 |
| WO | WO-2005/104994 | 11/2005 |
| WO | WO-2006/040759 | 4/2006 |
| WO | WO-2006/103674 | 10/2006 |
| WO | WO 2008/023379 | 2/2008 |
| WO | WO 2008/097915 | 8/2008 |
| WO | WO 2008/107882 | 9/2008 |
| WO | WO 2010/010565 | 1/2010 |

OTHER PUBLICATIONS

Chu, Ralph Y. and Buliano, Megan, Accommodating IOLs by Y. Ralph Cu et al, Cataract & Refractive Surgery Today, May 2004.

* cited by examiner

ACCOMMODATING INTRAOCULAR LENS ASSEMBLIES AND ACCOMMODATION MEASUREMENT IMPLANT

CROSS-REFERENCE TO RELATED APPLICATIONS

This application is a national stage application of PCT/IL2005/000456 filed May 1, 2005 claiming priority to IL 161706 filed Apr. 29, 2004 and to U.S. 60/589,567 filed Jul. 21, 2004.

TECHNICAL FIELD

The invention pertains to accommodating intraocular lens assemblies and apparatus for measuring accommodation in an experimental set-up including an animal eye.

BACKGROUND OF THE INVENTION

Commonly owned PCT International Application No. PCT/IL02/00693 entitled Accommodating Lens Assembly and published under PCT International Publication No. WO 03/015669 illustrates and describes accommodating intraocular lens (hereinafter AIOL) assemblies, the contents of which are incorporated herein by reference. The AIOL assemblies include a haptics system adapted to be securely fixed in a human eye's annular ciliary sulcus at at least two spaced apart stationary anchor points so that it may act as a reference plane for an AIOL of continuously variable Diopter strength affected by a human eye's capsular diaphragm acting thereagainst from a posterior direction and under control of its sphincter-like ciliary body. The haptics system includes a rigid planar haptics plate with a telescoping haptics member for sliding extension. The haptics plate and the haptics member are preferably self-anchoring as illustrated and described in commonly owned PCT International Application No. PCT/IL02/00128 entitled Intraocular Lens and published under PCT International Publication No. WO 02/065951, the contents of which are incorporated herein by reference. However, the haptics systems are not readily foldable thereby requiring a relatively large incision for insertion of an AIOL assembly into a human eye. Still further, anterior movements of a human eye's capsular diaphragm may lead to bulging of an AIOL assembly in an anterior direction instead of affecting an AIOL's Diopter strength. Moreover, the AIOL assemblies do not afford in situ re-adjustment along a human eye's visual axis which may be required due to capsular contraction thereby requiring that a subject resort to wearing spectacles or undergoing a surgical procedure for correcting his eyesight.

U.S. Pat. No. 6,739,722 to Laguette et al. illustrates and describes apparatus for measuring accommodation of a human eye including a target, a Badal lens, and a viewing aperture where the Badal lens and the viewing aperture are positioned so that when the target moves towards or away from the lens, the apparent size of the target remains constant to a subject looking in the viewing aperture regardless of the distance the target moves.

BRIEF SUMMARY OF THE INVENTION

Generally speaking, the present invention pertains to AIOL assemblies for self-anchoring implantation in a human eye's annular ciliary sulcus at least two and preferably more spaced apart stationary anchor points and having an AIOL of variable Diopter strength capable of in situ selective displacement along the human eye's visual axis for enabling accurate eyesight correction in general, and for compensating for capsular contraction in particular. The AIOLs include at least one shape memory optical element resiliently elastically deformable between a natural shape with a first Diopter strength and a deformed shape with a second Diopter strength different than the first Diopter strength whereby the AIOL has a continuously variable Diopter strength between a minimum Diopter strength for distance vision purposes and a maximum Diopter strength for near vision purposes. The first Diopter strength can be greater than the second Diopter strength or vice versa.

The AIOL assemblies can be implemented in either a two component construction including a discrete haptics system for selectively retaining a discrete AIOL or a unitary construction including a haptics system integrally formed with an AIOL. Axial re-positioning of a two component AIOL assembly involves displacement of its AIOL relative to its haptics system which remains stationary relative to its stationary anchor points. Against that, axial re-positioning of a unitary AIOL assembly involves adjusting the position of the portion of its haptics system holding its AIOL relative to its stationary anchor points. In the latter case, this is achieved by the haptics system including haptics plastically deformable on heating to a so-called glass transition temperature higher than a human eye's normal 36° C. temperature but sufficiently low not to damage a human eye's internal structures by irradiation with selective electromagnetic radiation.

The present invention also pertains to an accommodation measurement implant (AMI) for determining accommodation and the accommodation forces in an experimental set-up including an animal eye.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF THE INVENTION

Figure 1:
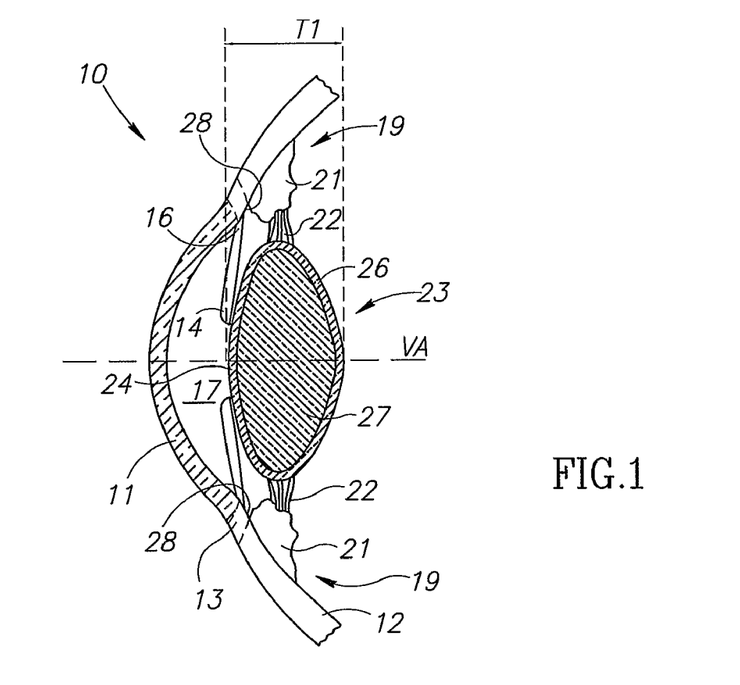
FIG. 1 is a cross section view of an anterior part of a human eye in its natural near vision condition in an axial plane of the human body.
Figure 2:
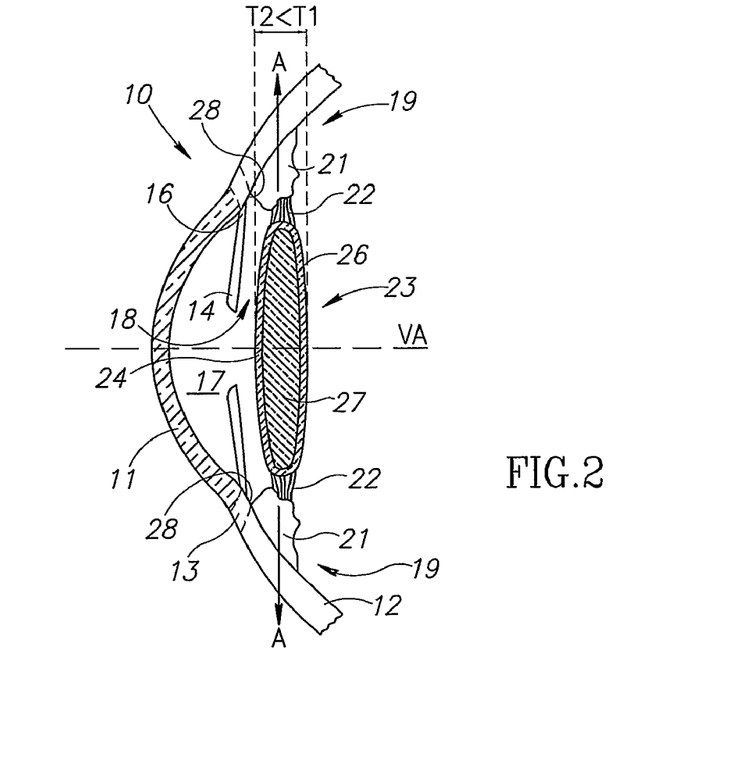
FIG. 2 is a cross section view of an anterior part of a human eye in its natural distance vision condition in an axial plane of the human body.

FIGS. 1 and 2 are cross section views of an anterior part of a human eye 10 having a visual axis VA in its natural near and distance vision conditions, respectively, in an axial plane of the human body. The human eye 10 has a cornea 11 peripherally connected to a spherical exterior body made of tough connective tissue known as the sclera 12 at an annular sclero-corneal juncture 13. An iris 14 inwardly extends into the human eye 10 from its root 16 at the sclero-corneal juncture 13 to divide the human eye's anterior part into an anterior chamber 17 and a posterior chamber 18. A sphincter-like peripheral structure known as the ciliary body 19 includes ciliary processes housing ciliary muscles 21 fired by parasympathetic nerves. The ciliary muscles 21 are connected to zonular fibers 22 which in turn are peripherally connected to the equatorial edge of a membrane known as the capsular bag 23 with an anterior capsule 24 and a posterior capsule 26 enrobing a natural crystalline lens 27. The iris's root 16 and the ciliary body 19 delimit a portion of the interior surface of the sclera 12 at the sclero-corneal juncture 13 known as the ciliary sulcus 28. Remnants of the anterior capsule 24 which may remain after extraction of the natural crystalline lens 27 and the intact posterior capsule 26 are referred to hereinafter as the capsular diaphragm 29. Contraction of the ciliary body 19 allows the lens 27 to thicken to its natural thickness T1 along the visual axis VA for greater positive optical power for near vision (see FIG. 1). Relaxation of the ciliary body 19 tensions the zonular fibers 22 which draws the capsular bag 23 radially outward as shown by arrows A for compressing the lens 27 to shorten its thickness along the visual axis VA to T2<T1 for lower positive optical power for distance vision (see FIG. 2).

Figure 3:
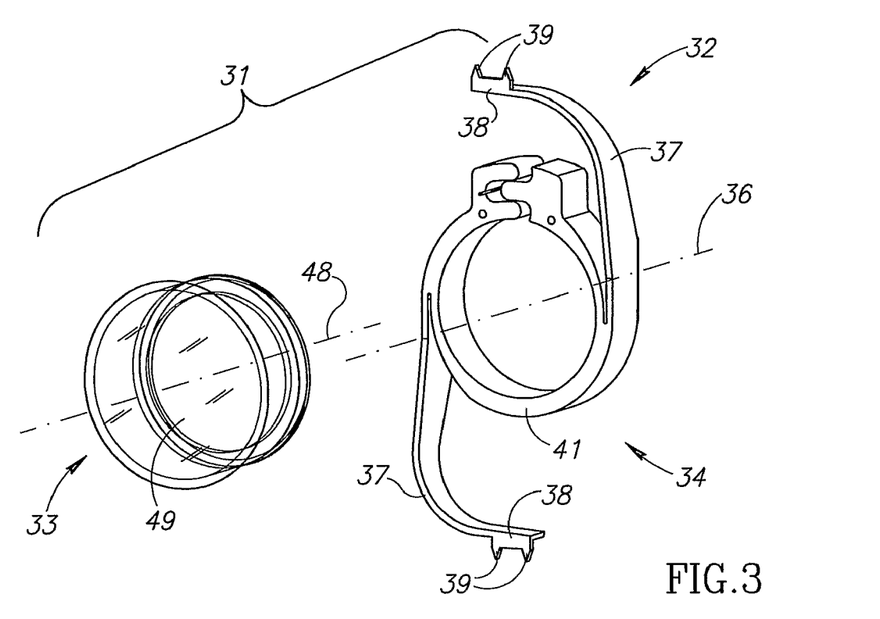
FIG. 3 is an exploded perspective view of a two component AIOL assembly including a discrete haptics system and a discrete natural low Diopter strength AIOL in accordance with the present invention.
Figure 4:
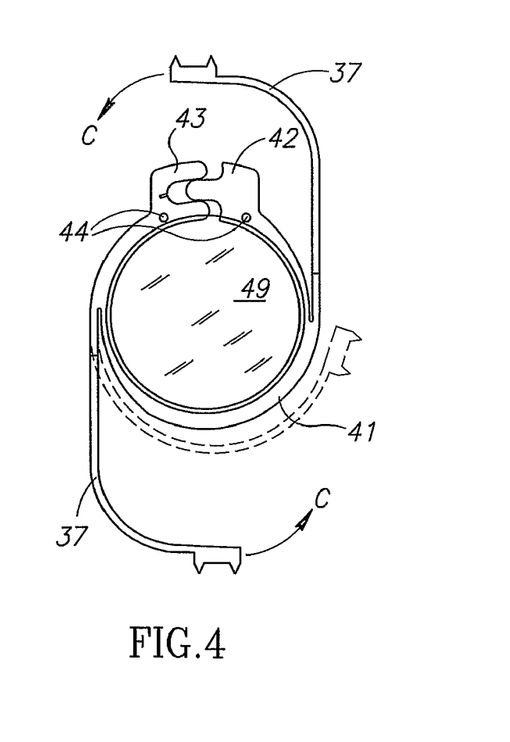
FIG. 4 is an assembled front view of FIG. 3's AIOL assembly.
Figure 5:
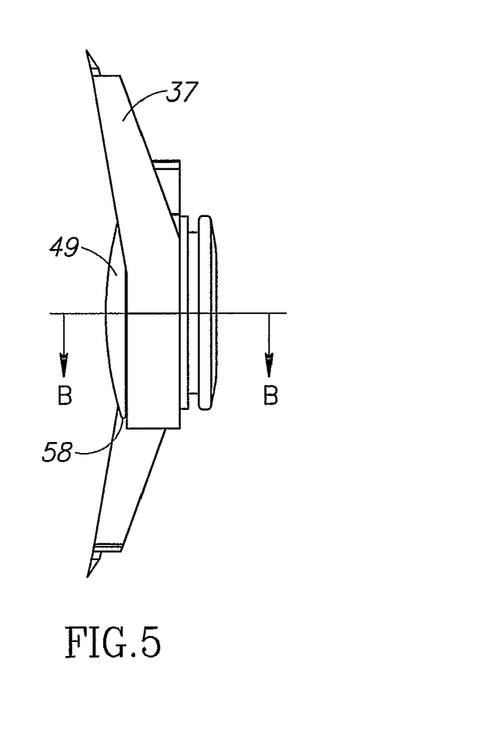
FIG. 5 is an assembled side view of FIG. 3's AIOL assembly.

FIGS. 3-5 show a two part AIOL assembly 31 made from suitable bio-compatible material such as PMMA, and including a haptics system 32 for self-anchoring implantation in a human eye's ciliary sulcus 28 for retaining an AIOL 33 therein for enabling spectacle free vision over the nominal range of human vision. The haptics system 32 includes a tubular main body 34 with an axial length L1 along a longitudinal axis 36 (see FIG. 6), and a pair of diametrically opposite haptics 37 tangentially extending therefrom in opposite directions in a front view of the haptics system 32. The haptics 37 have a pair of parallel and opposite attachment plates 38 with pointed penetrating members 39 of sufficient strength for forced penetration into the tough connective tissue of a human eye's sclera 12. The penetrating members 39 are preferably dimensioned so as to penetrate slightly more than half of a sclera's thickness of about 1 mm.

The main body 34 is in the form of a flexible split ring 41 with a male end 42 for releasable interference fit into a complementary female end 43 such that the main body 34 is capable of assuming a clamping state for tightly clamping the AIOL 33 therein. The male end 42 and the female end 43 are each provided with an axially directed bore 44 such that the split ring 41 can be prized apart by a suitable ophthalmic surgical tool (not shown) to an unclamping state for enabling axial displacement of the AIOL 33 for positioning purposes for compensating for capsular contraction, its entire replacement if necessary, and the like.

The haptics 37 have a thin profile in a plane perpendicular to the longitudinal axis 36 such that they are sufficiently flexible for encircling around the main body 34 in a direction shown by arrow C for facilitating insertion of the haptics system 32 through a relatively small incision into a human eye. FIG. 4 includes a haptics 37 in dotted lines for showing its encircling around the main body 34. The haptics 37 have a wide profile along the longitudinal axis 36 such that they are rigid against a compressive force therealong. The wide profile preferably tapers from a haptics' proximal end 37A adjacent the main body 34 towards its distal end 37B remote therefrom.

The AIOL 33 includes a tubular casing 47 with an axial length L2 along a longitudinal axis 48, a leading optically clear aperture lens 49 with an anterior surface 51, and a trailing flange 52. The casing's axial length L2 is longer than the main body's axial length L1 such that the main body 34 is capable of fully contacting the casing 47 along an adjustment stroke longer than the main body's axial length L1. The casing 47 slidingly supports a tubular piston-like member 53 with a leading flange 54 and a trailing flange 56 acting as a posterior surface against which a human eye's capsular diaphragm 29 bears. The AIOL 33 houses a shape memory optical element 57 made from soft gel or a fluid or gas filled membrane. The soft gel or fluid may be silicone based or water based, for example, Balanced Salt Solution (B SS), or any other biocompatible transparent liquid having a refractive index similar to that of the natural crystalline lens 27 or greater. The AIOL 33 includes a flange 58 for abutting against the main body 34 to stop displacement of the AIOL 33 in a posterior direction.

Figure 6:
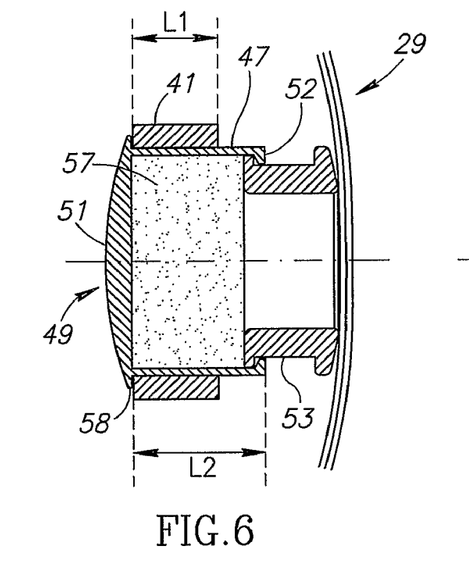
FIG. 6 is a longitudinal cross section view of FIG. 3's AIOL in its natural extended position along line B-B in FIG. 5.

The optical element 57 has a natural disc shape with a natural low Diopter strength for distance vision purposes and which urges the piston-like member 53 to a natural extended position (see FIG. 6). The optical element 57 is capable of being resiliently elastically deformed to a deformed shape by a force imparted by a human eye's capsular diaphragm on relaxation of its ciliary body acting against the piston-like member 53 in an anterior direction such that the piston-like member 53 assumes a compressed position with some of the optical element 57 bulging thereinto for rendering a high Diopter strength for near vision purposes (see FIG. 7). The piston-like member 53 is urged from its compressed position outwards to its natural extended position by the optical element 57 reverting to its natural shape on constriction of a human eye's ciliary body. Thus, the AIOL has a continuous variable Diopter strength between a minimum Diopter strength suitable for distance vision purposes and a maximum Diopter strength suitable for near vision purposes depending on the degree of compression of the piston-like member 53 in the casing 47.

Figure 8:
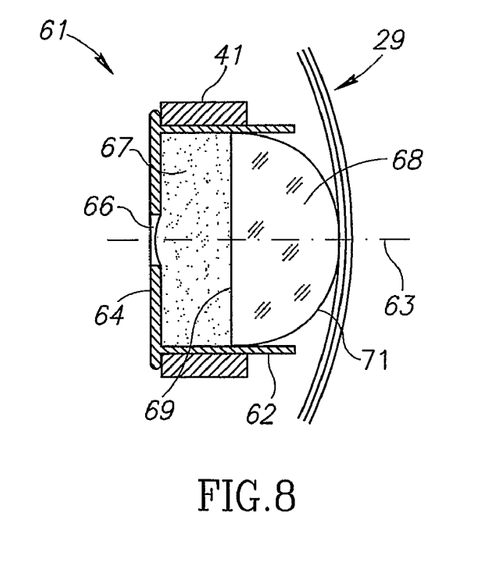
FIG. 8 is a longitudinal cross sectional view of another discrete natural low Diopter strength AIOL in its natural state in accordance with the present invention.

FIG. 8 shows an AIOL 61 also suitable for deployment in the haptics system 32 for correcting human eyesight. The AIOL 61 includes a tubular casing 62 with a longitudinal axis 63, and a flat aperture lens 64 constituting an anterior surface and having a central aperture 66. The casing 62 houses a shape memory optical element 67 of a natural disc shape, and a semi-spherical transparent piston-like member 68 having a flat surface 69 juxtaposed against the optical element 67 and a convex shaped posterior surface 71 against which a human eye's capsular diaphragm 29 directly bears for affecting the AIOL's Diopter strength. The optical element 67 has a natural low Diopter strength and is capable of being resiliently elastically deformed to a deformed shape with some of it bulging through the central aperture 66 on relaxation of a human eye's ciliary body for increasing the AIOL's Diopter strength.

Figure 9:
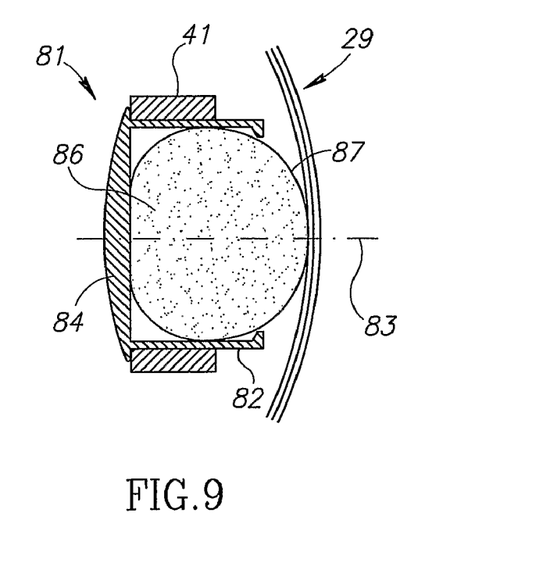
FIG. 9 is a longitudinal cross sectional view of a natural discrete high Diopter strength AIOL in its natural state in accordance with the present invention.

FIG. 9 shows an AIOL 81 also suitable for deployment in the haptics system 32 for correcting eyesight. The AIOL 81 includes a tubular casing 82 with a longitudinal axis 83, and a piano-convex aperture lens 84 constituting an anterior surface. The casing 82 houses a shape memory optical element 86 with a natural spherical shape and a posterior surface 87 against which a human eye's capsular diaphragm 29 directly bears for affecting the AIOL's Diopter strength. The optical element 86 has a natural high Diopter strength and is capable of being resiliently elastically deformed to a compressed shape on relaxation of a human eye's ciliary body urging its capsular diaphragm 29 against the posterior surface 87 in an anterior direction for decreasing the AIOL's Diopter strength in a similar fashion as the natural crystalline lens 27.

Figure 7:
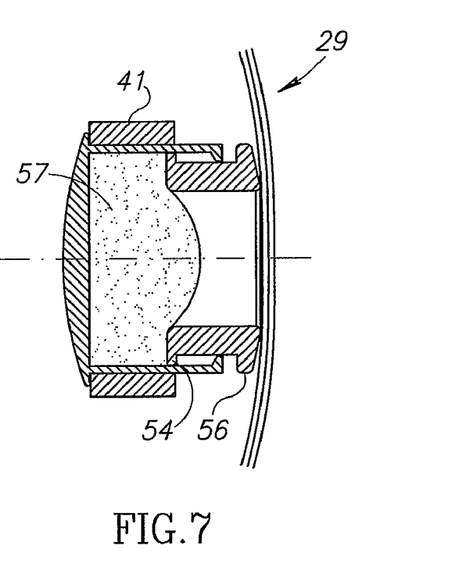
FIG. 7 is a longitudinal cross section view of FIG. 3's AIOL in a compressed position along line B-B in FIG. 5.
Figure 10:
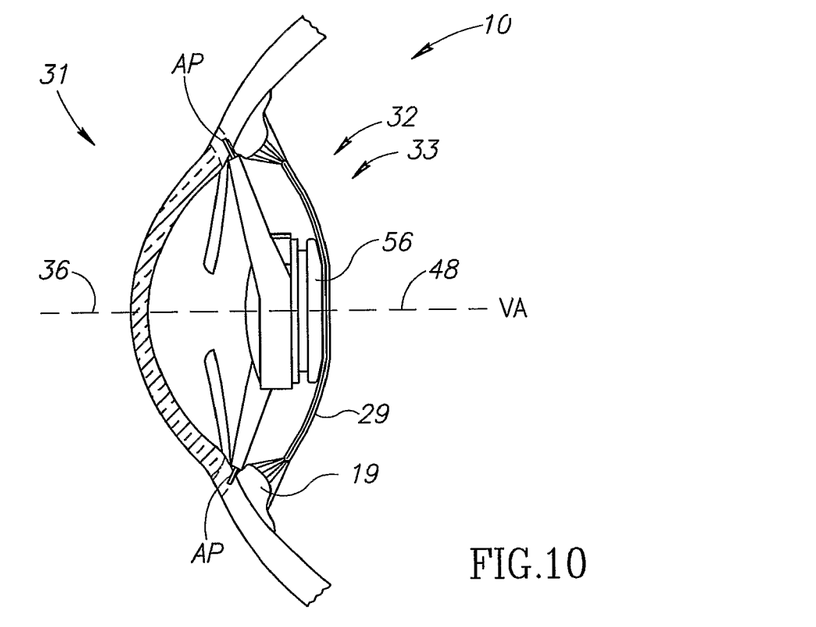
FIG. 10 is a cross section view of an anterior part of a human eye showing an initial position of FIG. 3's AIOL assembly along the human eye's visual axis in an axial plane of the human body.
Figure 11:
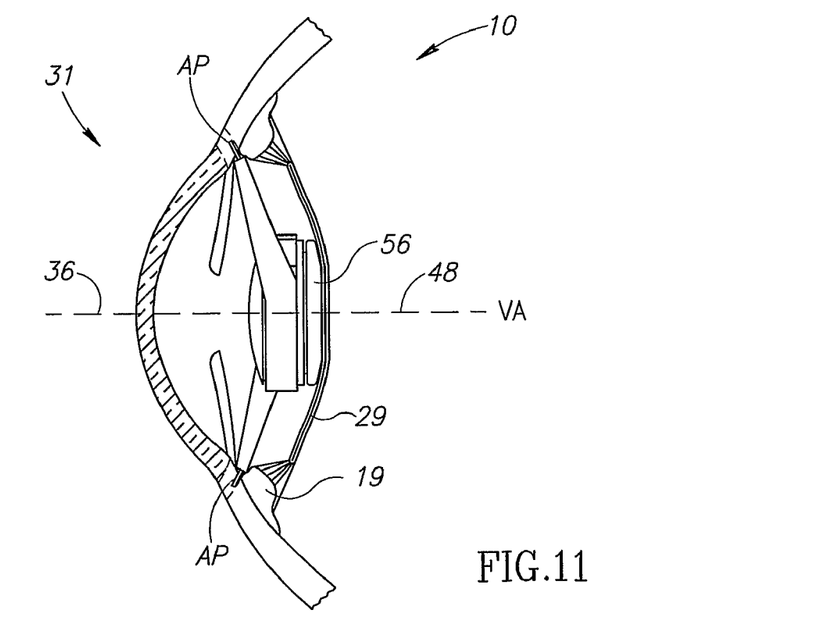
FIG. 11 is a cross section view of an anterior part of a human eye showing a subsequent position of FIG. 3's AIOL assembly along the human eye's visual axis for compensating for capsular contraction in an axial plane of the human body.
Figure 12:
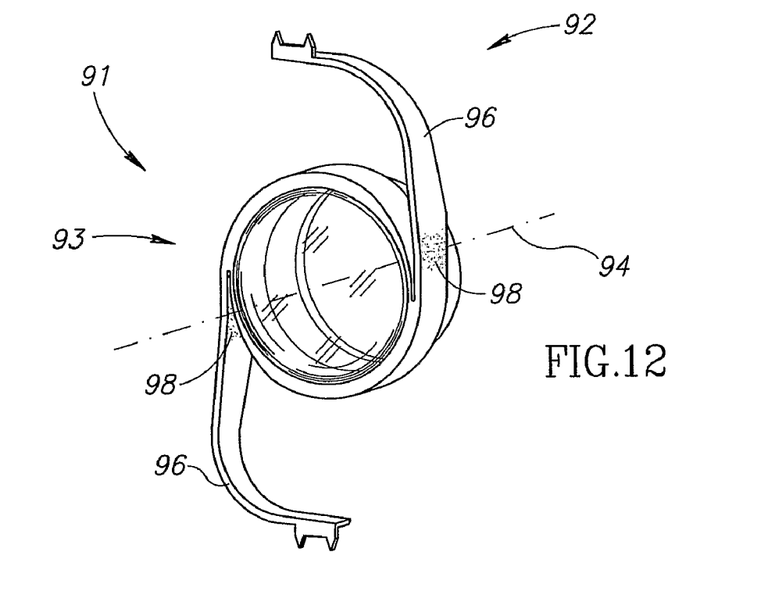
FIG. 12 is a perspective view of a unitary AIOL assembly in accordance with the present invention.
Figure 13:
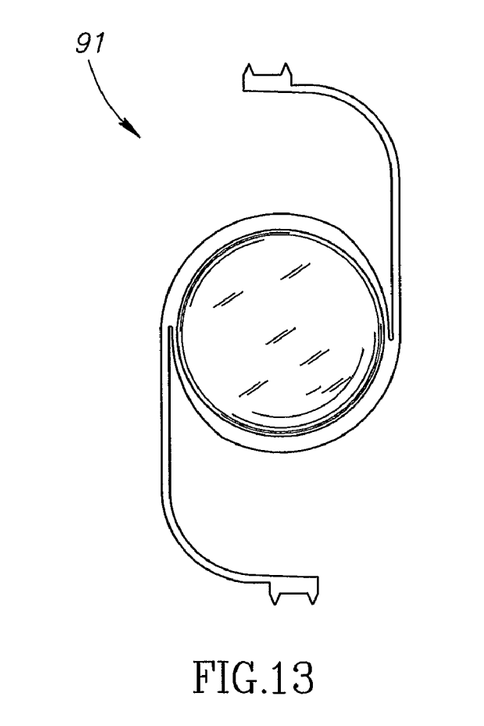
FIG. 13 is a front view of FIG. 12's AIOL assembly.
Figure 14:
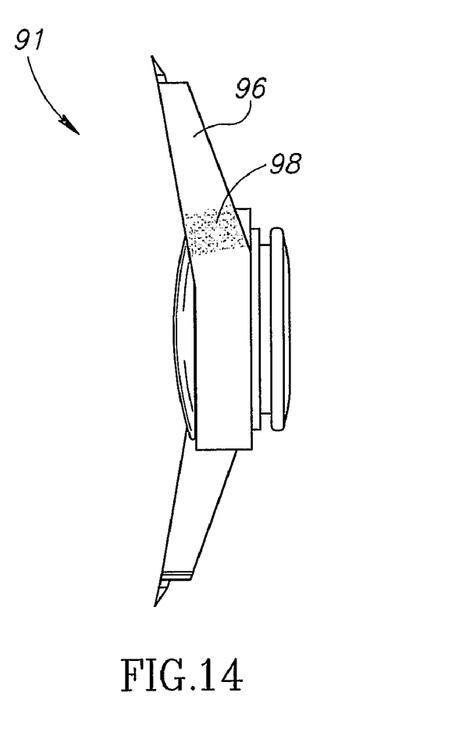
FIG. 14 is a side view of FIG. 12's AIOL assembly.
Figure 15:
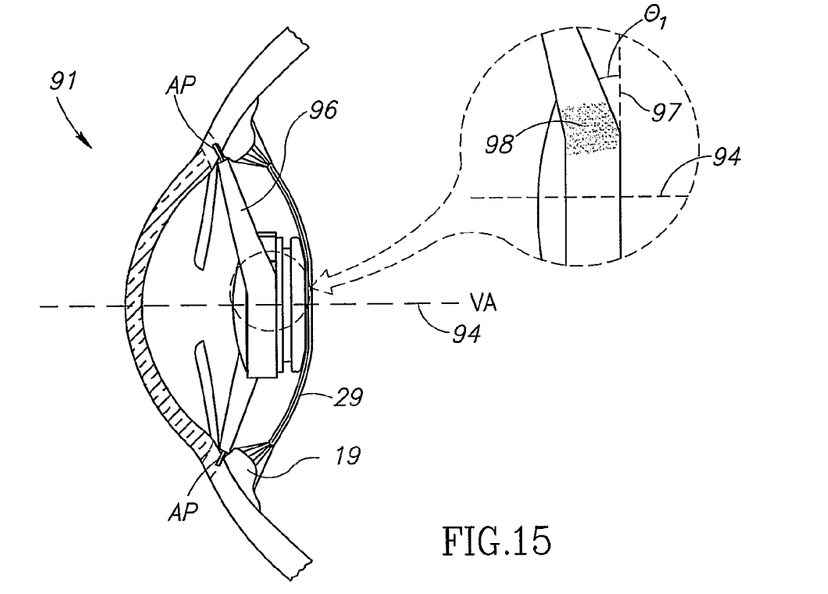
FIG. 15 is a cross section view of an anterior part of a human eye showing an initial position of FIG. 12's AIOL assembly along the human eye's visual axis in an axial plane of the human body.
Figure 16:
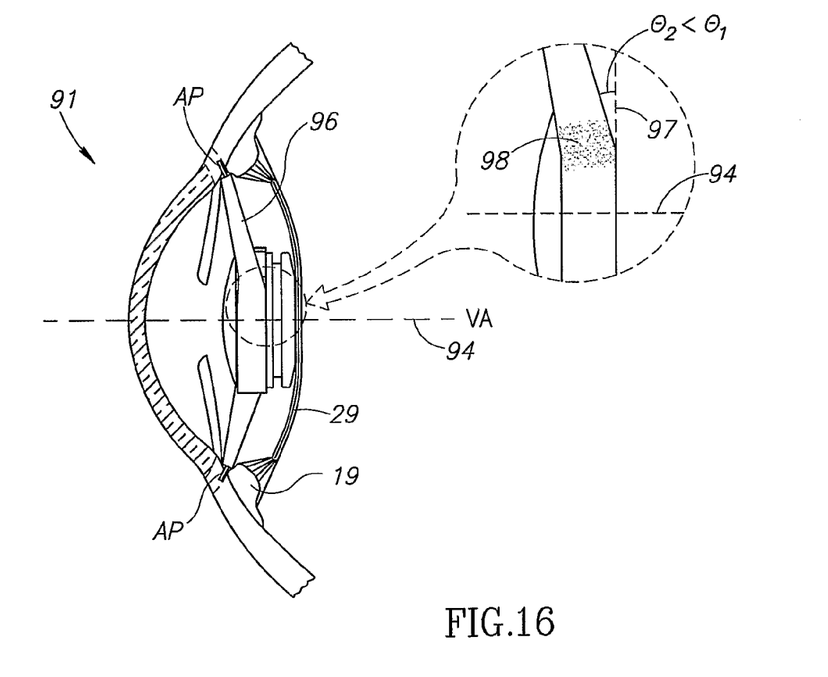
FIG. 16 is a cross section view of an anterior part of a human eye showing a subsequent position of FIG. 12's AIOL assembly along the human eye's visual axis for compensating for capsular contraction in an axial plane of the human body.

The implantation of an AIOL assembly of a variable Diopter strength in a human eye 10 after removal of its natural crystalline lens 27 is now described in connection with the AIOL assembly 31 with reference to FIGS. 10 and 11. The AIOL assembly 31 is set up such that the AIOL's longitudinal axis 48 coincides with the haptics system's longitudinal axis 36 and the annular flange 58 abuts against the main body 34 as shown in FIG. 6. The AIOL assembly 31 is typically implanted into a human eye 10 after administration of a suitable muscle relaxant for relaxing both its ciliary muscles and its iris muscles thereby dilating its pupil. The capsular diaphragm 29 has some slack by virtue of the removal of the natural crystalline lens 27. FIG. 10 shows that the haptics system's puncturing members 39 are forcibly inserted into the sclera 12 at stationary anchor points AP for retaining the AIOL assembly 31 in the annular ciliary sulcus 28. FIG. 10 also shows that the AIOL assembly 31 is deployed such that its longitudinal axes 36 and 48 are co-directional and preferably co-axial with the visual axis VA and the trailing flange 56 is urged in a posterior direction against the capsular diaphragm 29 tensioning same to become sufficiently taut to urge the AIOL 33 to its extreme compressed position as shown in FIG. 7 with maximum Diopter strength suitable for near vision purposes. Constriction of the ciliary body 19 enables the AIOL 33 to assume its extreme extended position as shown in FIG. 6 with minimum Diopter strength suitable for distance vision purposes. In the case of capsular contraction, the AIOL 33 is unable to assume its extreme extended position but rather it remains at least partially compressed depending on the degree of the capsular contraction thereby diminishing its accommodation ability. The accommodation ability of the AIOL 33 is restored by prizing open the split ring 41 and moving the AIOL 33 in an anterior direction as evidenced by the gap between the AIOL's flange 58 and the split ring 41 as seen in FIG. 11.

FIGS. 12-16 show an AIOL assembly 91 which is similar to the AIOL assembly 31 but differs therefrom in two respects: First, the AIOL assembly 91 is unitary insofar that it includes a haptics system 92 for self-anchoring implantation in a human eye's ciliary sulcus 28 at least two stationary anchor points AP integrally formed with an AIOL 93 of variable Diopter strength. And second, the haptics system 92 has a longitudinal axis 94 and includes a pair of haptics 96 which are capable of being plastically deformed from an initial acute angle $\theta_1$ (see FIG. 15) subtended with respect to a plane 97 perpendicular to the longitudinal axis 94 to a less acute angle $\theta_2 < \theta_1$ (see FIG. 16) such that the haptics system 92 is capable of in situ selective displacement of the AIOL 93 from an initial position to a desired position along a human eye's visual axis VA. This is achieved by the haptics 96 having regions 98 adjacent the AIOL 93 impregnated with radiation sensitive bio-compatible chemicals, for example, Infra Red (IR) sensitive indocyanine green (ICG), and the like, such that the haptics 96 are plastically deformable on heating to a so-called glass transition temperature higher than a human eye's normal 36° C. temperature but sufficiently low so as to not damage a human eye's delicate internal structures.

Figure 17:
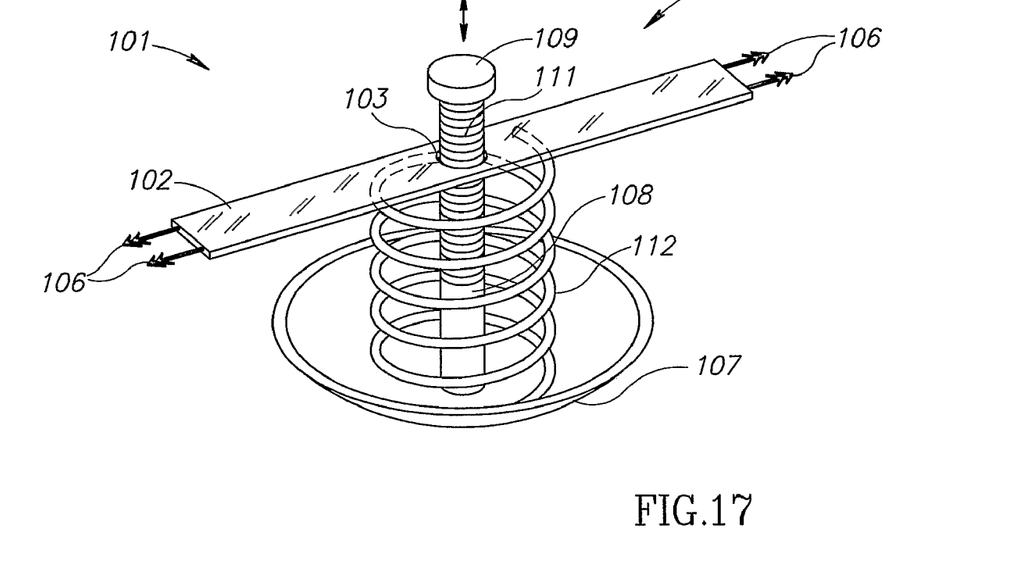
FIG. 17 is a perspective view of an accommodation measurement implant for measuring accommodation and accommodation forces in an experimental set-up including an animal eye.
Figure 18:
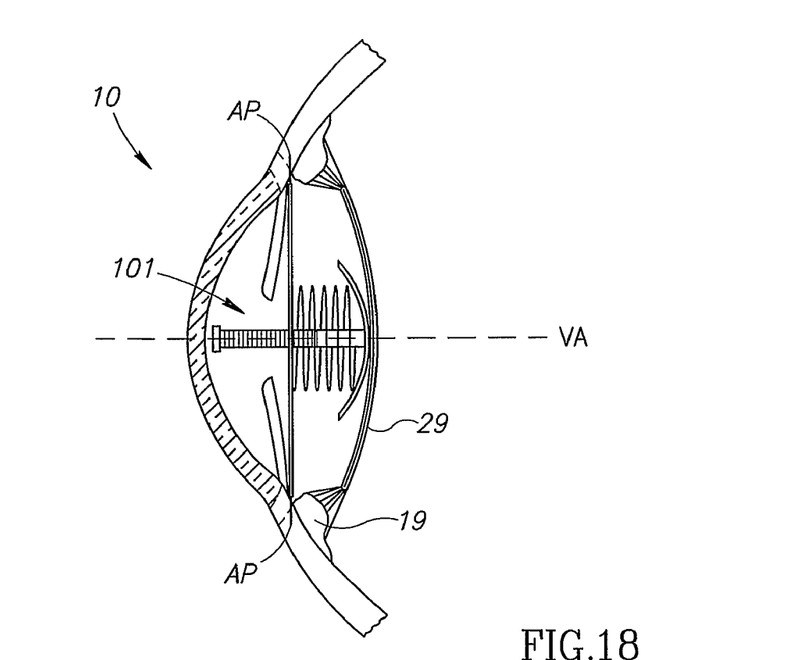
FIG. 18 is a cross section view showing deployment of the accommodation measurement implant of FIG. 17.

FIGS. 17 and 18 show an accommodation measurement implant (AMI) 101 for determining accommodation and accommodation forces in an experimental set-up including an animal eye similar to a human eye and therefore likewise numbered. The AMI 101 includes a generally rectangular rigid planar base member 102, and a central aperture 103. The base member 102 includes a haptics system 104 in the form of oppositely directed pointed puncturing members 106 for self-anchoring at anchor points AP. A convex shaped member 107 suitably shaped and dimensioned for placing on an animal eye's capsular diaphragm 29 from the anterior direction is provided with an upright pin 108 having a pinhead 109 and passing through the aperture 103. The pin 108 includes a series of graduations 111 therealong at a pitch of less than 500 μm, and preferably at 250 μm. A helical compression spring 112 is placed between the base member 102 and the convex shaped member 207 for urging them apart to be stopped by the pinhead 109 abutting against the base member 102. The base member 102, the convex shaped member 107, and the pin 108 are preferably formed of a suitable biocompatible material, for example, stainless steel, PMMA, and the like. Accommodation is determined as a function of a pin's displacement relative to the base member 102 as a result of relaxation of the ciliary body 19. Pin displacements may be detected by external devices or alternatively the graduations 111 may be inspected by a direct eye inspection. The actual forces developed by the relaxation of a ciliary body can be determined as a function of the compression spring's spring constant k and pin displacement.

While the invention has been described with respect to a limited number of embodiments, it will be appreciated that many variations, modifications, and other applications of the invention can be made within the scope of the appended claims.

What is claimed is:

1. An accommodating intraocular lens (AIOL) assembly for self-anchoring implantation in a human eye having a visual axis, a sclera of tough connective tissue, an annular ciliary sulcus, and a sphincter-like ciliary body having a relaxed state for tensioning a capsular diaphragm in an anterior direction along the visual axis, the AIOL assembly comprising:

a) an accommodating intraocular lens (AIOL) having an anterior surface and a posterior surface, and at least one shape memory optical element resiliently elastically deformable between a natural shape with a first Diopter strength and a deformed shape with a second Diopter strength different than said first Diopter strength whereby said AIOL has a continuously variable Diopter strength between a minimum Diopter strength for distance vision purposes and a maximum Diopter strength for near vision purposes; and b) a haptics system including a main body formed of a rigid material with a longitudinal axis intended to be co-directional with the human eye's visual axis and at least two haptics each with at least one pointed puncturing member capable of penetrating the tough connective tissue of the human eye's sclera for self-anchoring implantation of said haptics system in the human eye's annular ciliary sulcus, at least two spaced apart stationary anchor points adaatedt to retain said AIOL along the human eye's visual axis at an in situ manually selectively displaceable desired position there along relative to said at least two stationary anchor points so that said haptics system is capable of urging said posterior surface against the human eye's capsular diaphragm from an anterior direction for determining said AIOL's Diopter strength at said desired position, said haptics system including a portion that is capable of being physically altered for adjustment of said AIOL relative to said anchor points after implantation, whereupon relaxation of the human eye's ciliary body is capable of urging the human eye's capsular diaphragm against said posterior surface from a posterior direction for affecting said AIOL's Diopter strength.

2. The assembly according to claim 1 wherein said haptics system includes a tubular main body stationary relative to said at least two spaced apart stationary anchor points, and is capable of being in situ selectively manipulated between a clamping state for retaining a discrete AIOL having a tubular casing with a longitudinal axis at a desired position along the human eye's visual axis and an unclamping state for enabling said discrete AIOL to be selectively displaced relative to said stationary haptics system to a desired position along the human eye's visual axis.

3. The assembly according to claim 2 wherein said main body has an axial length L1 along its longitudinal axis and said casing has an axial length L2 along its longitudinal axis where L2>L1 such that said main body is capable of fully contacting said casing in said clamping state along an adjustment stroke longer than said main body's axial length.

4. The assembly according to claim 3 wherein said AIOL includes a flange for abutting against said main body to stop displacement of said AIOL in a posterior direction.

5. The assembly according to claim 1 wherein said haptics system is integrally formed with said AIOL and said at least two haptics each include a radiation sensitive region capable of plastic deformation on in situ irradiation with selective electromagnetic radiation for enabling in situ selective displacement of said integrally formed AIOL to a desired position along the human eye's visual axis relative to said at least two spaced apart stationary anchor points.

6. The assembly according to claim 5 wherein said radiation sensitive region is adjacent said main body.

7. The assembly according to claim 5 wherein said AIOL includes a piston-like member reciprocable between a natural extended position corresponding to said first Diopter strength and a compressed position corresponding to said second Diopter strength.

8. The assembly according to claim 5 wherein said AIOL has a natural low Diopter strength and relaxation of the human eye's ciliary body increases said AIOL's Diopter strength.

9. The assembly according to claim 5 wherein said AIOL has a natural high Diopter strength and relaxation of the human eye's ciliary body decreases said AIOL's Diopter strength.

10. The assembly according to claim 5 wherein each haptics of said at least two haptics has a thin profile in a plane perpendicular to said haptics system's longitudinal axis such that said at least two haptics are sufficiently flexible for encircling around said main body, and a wide profile along said haptics system's longitudinal axis such that said at least two haptics are rigid against a compressive force therealong.

11. The assembly according to claim 10 wherein said wide profile tapers from a haptics' proximal end adjacent said main body towards its distal end remote therefrom.

12. A discrete accommodating intraocular lens (AIOL) for implantation in a human eye having a visual axis, a sclera of tough connective tissue, an annular ciliary sulcus, and a sphincter-like ciliary body having a relaxed state for tensioning a capsular diaphragm in an anterior direction along the visual axis, a discrete haptics system having a tubular main body formed of a rigid material with a longitudinal axis and at least two haptics each with at least one pointed puncturing member capable of penetrating the tough connective tissue of the human eye's sclera for self-anchoring implantation in the human eye's annular ciliary sulcus, at least two spaced apart stationary anchor points adapted to retain the AIOL along the human eye's visual axis at an in situ selectively displaceable desired position therealong relative to the at least two spaced apart stationary anchor points, the AIOL comprising a discrete tubular casing having a longitudinal axis, an anterior surface and a posterior surface, and at least one shape memory optical element resiliently elastically deformable between a natural shape with a first Diopter strength and a deformed shape with a second Diopter strength different than said first Diopter strength whereby the AIOL has a continuously variable Diopter strength between a minimum Diopter strength for distance vision purposes and a maximum Diopter strength for near vision purposes;

said posterior surface being capable of being urged against the human eye's capsular diaphragm from an anterior direction for determining the AIOL's Diopter strength at the desired position such that relaxation of the human eye's ciliary body urges the human eye's capsular diaphragm against said posterior surface from a posterior direction for affecting said AIOL's Diopter strength, the haptics system including a portion that is capable of being physically altered for adjustment of said AIOL relative to the anchor points after implantation, whereupon relaxation of the human eye's ciliary body is capable of urging the human eye's ciliary body capsular diaphragm against said posterior surface from a posterior direction for affecting said AIOL's Diopter strength.

13. The AIOL according to claim 12 wherein the haptics system's main body has an axial length L1 along its longitudinal axis and said casing has an axial length L2 along its longitudinal axis wherein L2>L1 such that the haptics system's main body is capable of fully contacting said casing along an adjustment stroke longer than the main body's axial length L1.

14. The AIOL according to claim 12 wherein said casing slidingly supports a piston-like member between a natural extended position corresponding to said first Diopter strength and a compressed position corresponding to said second Diopter strength.

15. The AIOL according to claim 12 and further comprising a flange for abutting against the haptics system to stop displacement of the AIOL in a posterior direction.

16. The AIOL according to claim 12 wherein said AIOL has a natural low Diopter strength and relaxation of human eye's ciliary body increases the AIOL's Diopter strength.

17. The AIOL according to claim 12 wherein said AIOL has a natural high Diopter strength and relaxation of the human eye's ciliary body decreases the AIOL's Diopter strength.

18. The assembly according to claim 2 wherein said AIOL includes a piston-like member reciprocable between a natural extended position corresponding to said first Diopter strength and a compressed position corresponding to said second Diopter strength.

19. The assembly according to claim 2 wherein said AIOL has a natural low Diopter strength and relaxation of the human eye's ciliary body increases said AIOL's Diopter strength.

20. The assembly according to claim 2 wherein said AIOL has a natural high Diopter strength and relaxation of the human eye's ciliary body decreases said AIOL's Diopter strength.

21. The assembly according to claim 2 wherein each haptics of said at least two haptics has a thin profile in a plane perpendicular to said haptics system's longitudinal axis such that said at least two haptics are sufficiently flexible for encircling around said main body, and a wide profile along said haptics system's longitudinal axis such that said at least two haptics are rigid against a compressive force therealong.

22. The assembly according to claim 21 wherein said wide profile tapers from a haptics' proximal end adjacent said main body towards its distal end remote therefrom.

23. The assembly of claim 1, wherein said portion that is capable of being physically altered comprises said main body being formed of a split ring which can be opened and closed to allow said AIOL to move along the visual axis relative to said main body.

24. The AIOL according to claim 12 wherein said AIOL includes a flange for abutting against said main body to stop displacement of said AIOL in a posterior direction.

25. The AIOL according to claim 12, wherein said portion that is capable of being physically altered comprises said main body being formed of a split ring which can be opened and closed to allow the AIOL to move along the visual axis relative to said main body.

* * * * *

UNITED STATES PATENT AND TRADEMARK OFFICE
CERTIFICATE OF CORRECTION

| | | |
|---|---|---|
| PATENT NO. | : 7,842,087 B2 | Page 1 of 1 |
| APPLICATION NO. | : 11/568416 | |
| DATED | : November 30, 2010 | |
| INVENTOR(S) | : Yehoshua Ben Nun | |

It is certified that error appears in the above-identified patent and that said Letters Patent is hereby corrected as shown below:

Claim 1, Column 7, Line 18, delete "," and insert --at-- therefor

Claim 1, Column 7, Line 19, change --adaatedt-- to "adapted"

Claim 12, Column 8, Line 31, delete "," and insert --at-- therefor

Signed and Sealed this
Fifteenth Day of March, 2011

David J. Kappos
*Director of the United States Patent and Trademark Office*